United States Patent

Combs et al.

[11] Patent Number: 5,957,861
[45] Date of Patent: Sep. 28, 1999

[54] IMPEDANCE MONITOR FOR DISCERNING EDEMA THROUGH EVALUATION OF RESPIRATORY RATE

[75] Inventors: William J. Combs, Eden Prarie; Catherine R. Condie, Minneapolis; Roy Martin, Maple Grove; Dwight H. Warkentin, St. Paul; John D. Wahlstrandl, Shoreview, all of Minn.

[73] Assignee: Medtronic, Inc., Minneapolis, Minn.

[21] Appl. No.: 08/791,206

[22] Filed: Jan. 31, 1997

[51] Int. Cl.⁶ .................................................. A61B 5/00
[52] U.S. Cl. ..................... 600/547; 600/529; 600/481; 600/536; 607/6
[58] Field of Search .................... 607/1, 2, 6, 7, 607/9, 15, 16–18, 28–30, 32–37; 600/481, 483, 484, 508, 509, 513, 529, 536, 547, 573, 579

[56] References Cited

U.S. PATENT DOCUMENTS

| | | | |
|---|---|---|---|
| 4,576,183 | 3/1986 | Plicchi et al. | 128/723 |
| 4,987,897 | 1/1991 | Funke | 128/419 PG |
| 5,113,869 | 5/1992 | Nappholz et al. | 128/696 |
| 5,117,825 | 6/1992 | Grevious | 128/419 PG |
| 5,233,985 | 8/1993 | Hudrlik | 607/27 |
| 5,246,008 | 9/1993 | Mueller | 128/695 |
| 5,271,395 | 12/1993 | Wahlstrand et al. | 607/9 |
| 5,282,840 | 2/1994 | Hudrlik | 607/28 |
| 5,300,093 | 4/1994 | Koestner et al. | 128/419 |
| 5,313,953 | 5/1994 | Yomtov | 128/696 |
| 5,324,315 | 6/1994 | Grevious | 607/60 |
| 5,354,319 | 10/1994 | Wyborny | 607/32 |
| 5,370,665 | 12/1994 | Hudrlik | 607/9 |
| 5,411,031 | 5/1995 | Yomtov | 128/706 |
| 5,507,785 | 4/1996 | Deno | 607/24 |
| 5,534,018 | 7/1996 | Wahlstrand et al. | 607/27 |
| 5,732,710 | 3/1998 | Rabinovich et al. | 128/734 |
| 5,749,369 | 5/1998 | Rabinovich et al. | 128/734 |

FOREIGN PATENT DOCUMENTS

| | | | |
|---|---|---|---|
| 0 348 271 A1 | 12/1989 | European Pat. Off. | A61M 5/14 |
| WO 84/00227 | 1/1984 | WIPO | A61B 5/02 |

OTHER PUBLICATIONS

Transthoracic Electrical Impedance as a guide to intravascular Overload by Berman et al (archives surgery V102 PP61–64 Jan. 1997).

Effects of Prehospital Medications on Mortality and Length of stay in Congestive Heart Failure By Wuerz and Meador, (Annals of Emergency Medicine, 21:6 Jun. 1992 pp. 669–674).

Clinical Cardiac Pacing Kenneth EllenBogen et al published WB Saunders Co copyright 1995 pp. 219–233.

Rate Responsive Pacing with a Pacemaker that detects respiratory rate (Biorate) Vlinical advantages and complications by Lau et al, (Clinical Cardiology, May 1988 11 (5) pp. 318–324).

Primary Examiner—Robert L. Nasser
Attorney, Agent, or Firm—Harold R. Patton; Michael B. Atlass

[57] ABSTRACT

An impedance monitor for discerning edema through evaluation of respiratory rate. Preferred embodiment includes edema monitor and trigger to initiate diagnostic reporting or corrective action when activated. Recording of Long Term Average and Short Term Average values for secondary edema measure based on DC signal level are described as are methods and apparatus for removing unwanted recurring noise.

36 Claims, 9 Drawing Sheets

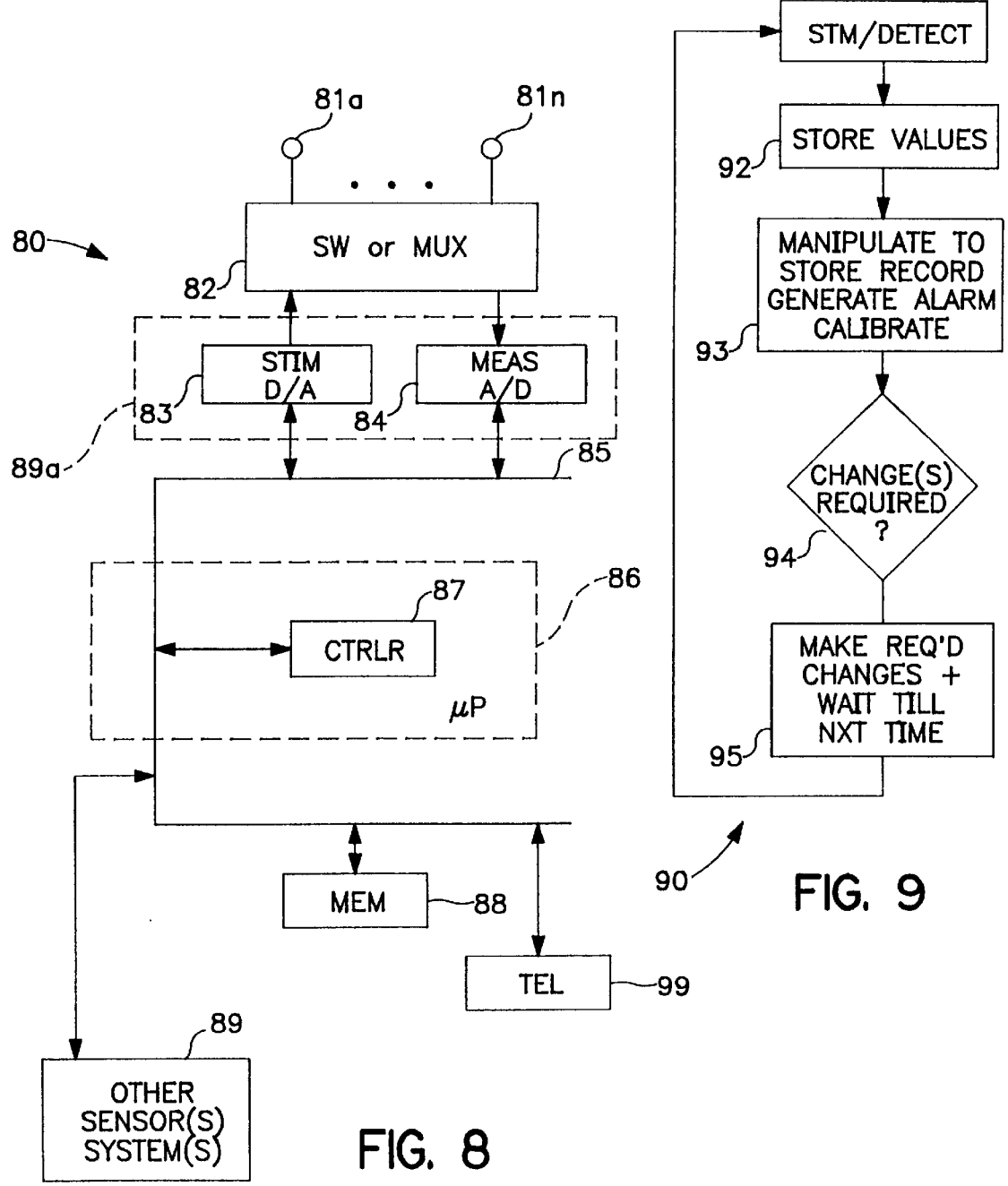

IMPEDANCE MONITOR FOR DISCERNING EDEMA THROUGH EVALUATION OF RESPIRATORY RATE

BACKGROUND

This invention relates to implantable devices including but not limited to tissue stimulators having measurement capability for determining impedance measurements and is particularly well suited to measure long term edema variations within a living body.

Impedance monitoring has been used for determination of numerous physiologic conditions within the body with implanted devices and has been used in external monitoring devices as well. It is commonly understood that Transthoracic Impedance measurements give a good indication of the level of edema in patients. Even as far back as 1971, in an article entitled "Transthoracic Electrical Impedance as a guide to Intravascular Overload" by Berman et. al. (Archives surgery, V102 P61–64 January 1971), electrical impedance methods have been used to document the accumulation of fluid in the living tissue.

What's important about long term impedance measurement and noting changes therein is that it is an valuable clinical indicator of the health of the living body which has heretofore been unavailable to physicians in a very useful form.

While edema is a sign of many other conditions it is also a sign of the failing heart circulation which is our first concern. There are several mechanisms or diseases that can cause or affect edema. In general edema is a failure or over response of homeostatic process within the body. The body normally prevents the build up of fluids by maintaining adequate pressures and concentrations of salt and proteins, and by actively removing excess fluid. If a disease affects any of these mechanisms the result can be edema. This includes heart failure, left sided MI(Myocardial Infarction), high blood pressure, altitude sickness, emphysema (all which affect pressures), and cancers that affect the lymphatic system, diseases which disrupt the protein concentrations, . . . etc. The list is large. The point is that by providing an adequate monitor of edema we can provide a physician and his patient with a better tool to manage disease.

Unfortunately, ordinarily the first indication that a treating physician would have of the occurrence of edema is very late in the disease process when it becomes a physical manifestation with swelling or breathing difficulties so overwhelming as to be noticed by the patient who then proceeds to be examined by a physician. For a cardiac heart failure (CHF) patient, hospitalization at such time would likely be required. A device and system as proposed in this application can obviate the need for proactive hospitalization simply to monitor a patient's progression of edema as hospital stays are discouraged whenever possible under the emerging health care delivery system in the world today. Therefore a strong incentive or need exists for devices that can allow a patient to be monitored for disease symptoms over a long term without requiring hospitalization and allows for out-of-hospital intervention when symptoms, in this case, due to edema suggest it.

Additional need for this type of invention is found in the article "EFFECTS OF PREHOSPITAL MEDICATIONS ON MORTALITY AND LENGTH OF STAY IN CONGESTIVE HEART FAILURE," by Wuerz and Meador, ANNALS OF EMERGENCY MEDICINE, 21:6, June, 1992, pp 669–74, in which it is demonstrated that early pre-hospital treatment can save lives. A device that establishes new indications before the patient can be hospitalized by allowing for a readout of accumulated and trend data can be seen as an improvement in the tools available to save lives from CHF.

There are numerous devices and teachings which describe or are capable of making impedance measurements including U.S. Pat. Nos. 5,534,018, 5,271,395, 5,370,6665, 5,233, 985, and 5,282,840. Likewise, there are numerous mentions of the use of impedance for determination of levels of edema in the literature without the use of long term implantable devices which usually require significant and expensive monitoring, attention, and effort. Such monitoring and effort may not be available before hospitalization. However, there currently are no impedance measurement devices suitable for providing an indication of when an edema is about to become a serious problem for a patient, nor for closely monitoring it over a protracted period of time. Consequently, as patients become out of titer on their edema management medication (diuretics, for example) or after they unknowingly or unintentionally eat salty foods, hospitalization may be enhanced or possibly avoided through the use of a device as described herein. Thus healthcare resources can be used more efficiently and effectively to help CHF patients in particular as well as other patients which can benefit from similar information availability.

It should be noted that adaptations of some technologies for performing some patient monitoring functions are developed as evidenced by U.S. Pat. Nos. et al, 5,313,953 and 5,411,031, to Yomotov, incorporated herein by reference in their entirieties. However as yet there has not been acceptance of implantable devices for monitoring purposes alone, and certainly none for simply monitoring edema per se, nor for edema as a partial indicator of health, nor for use of edema monitoring as an adjunct indicator for therapy modification. Accordingly it is believed there is a large need for the teaching of this invention.

Additional measurements—Respiration rate.

Additional data can be found in the respiration rate which can be monitored as a separate and independent indicator of edema onset and particularly of pulmonary edema or increased lung water, since patients are known to breath quickly when their lungs fill with fluid. It is known, for instance that in extreme cases of pulmonary edema breathing rates of 60 per minute can occur. Because it would be impossible to clinically measure slight changes in long term breathing rates, for example a 5.5 to 5.8 breath per minute change, but such monitoring is possible with an implanted device, by including a processor for sampling the rate of breathing and comparing it to next sampled rates over time, substantial clinical benefit can be obtained by making this data available.

BRIEF DESCRIPTION OF THE DRAWINGS

FIG. 8 is a circuit block diagram of a generalized version of this invention.

FIG. 9 is a flow diagram for a control for use with this invention.

SUMMARY OF THE INVENTION

Figure 1:
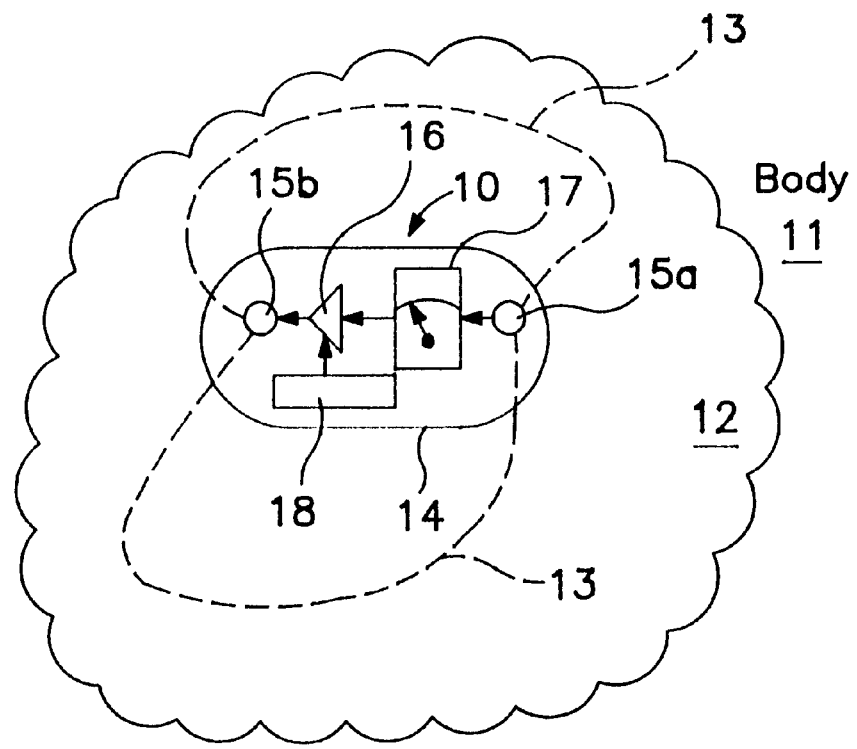
FIG. 1 is a cut away view of the body having a implanted impedance measurement device for monitoring impedance within a body in accord with this invention.

A system for determining, generating, monitoring, and using signal representative of edema in a living body is described herein.

It includes an implantable apparatus for production of impedance measurement in a subcutaneous region of the living body having at least two electrically isolated electrodes, preferably but not necessarily on the outer surface of its housing and having within the housing an energy pulse delivery mechanism to deliver electrical pulses to living body and means for receiving electrical impulses on the surface of the housing so as to determine the impedance of the body between the two preferred or less preferred pair of electrodes.

The energy pulse delivery mechanism may advantageously be provided with an adjustment control that can be used to customize the output for a patient, assist in optimization of the Signal to Noise Ratio (SNR), and avoid local muscle stimulation. Automatic feedback control loops may be used for this purpose, but in the presently preferred embodiment, both the determination of the preferred pulse delivery electrodes and the values used for the impedance energy pulse to initiate measurement are either factory set or controlled by a telemetry link to the implant during the implant or adjustment procedure.

This invention can be used in conjunction with traditional pacemaker systems and implantable defibrillators, and other implantable devices, or may be incorporated into them. For example, the electrode configuration for impedance measurement may include a cardiac electrode tip in the heart and an electrode on the surface of a pacemaker housing for one measure of impedance and an additional pair of electrodes both located on the housing would enable the use of two different measures of impedance and facilitate the use of comparisons between the resultant signals to refine the signal and provide additional information.

Additional means for discriminating impedance noise signals which are not representative of edema may be included within the housing. Apparatus and method for determining long term and short term average values (LTA and STA values, respectively) and also for determining when to sample impedance measurements are included. In preferred embodiments trigger means for determining diagnostically significant events based on long term and short term average values are also included.

Memory for storage and processors and signaling for managing the storage so that optimal diagnostic data can be stored based on edema measurement signals are also provided.

Enhancements include various ways to produce power within the device, programmable output values of impedance pulses, optimization of electrodes synchronization of stimulus pulses to physiologically recurring signals. Alarm means, base station means, telephonic links, and diagnostic assistance may also be additionally provided.

For instantiations where the invention is installed into pacemakers or drug pumps or other implantable devices, it can be used to alter the delivery of drugs and stimulation pulses to respond to the onset of edema automatically.

It is also possible to determine edema valuations from respiratory rate and such a mechanism can also be provided.

In Cardiac Heart Failure (CHF) patients the infusion of diuretics to manage edema automatically is a prime example of how this invention would be most useful.

Also, for providing additional useful data or for reference by automatic triggering apparatus to store data(in looping or non-looping memories) or generate alarms or take other actions based on significant events, ECG signal reading, pedal impact or other activity sensors, and sensors for measuring temperature, pressure, oxygen saturation, and so forth may advantageously be included. Where such triggers are used the device can be constructed to perform an appropriate device behavior from a range of preconditioned device behaviors.

DETAILED DESCRIPTION OF THE PREFERRED EMBODIMENTS

In the heuristic drawing of FIG. 1, a section of a Body 11 is shown with a cut-away area 12 to allow for illustration of the inventive device 10. The device 10 has two electrodes 15a and 15b on the surface of its shell 14. Power is provided to the circuitry internal to the shell 14 by a power supply 18 which drives a stimulation circuit 16 which sends electrons through various pathways in the body (such pathways are heuristically illustrated as being primarily in the area surrounded by dotted line)13 between electrodes 15a and 15b. An impedance measurement device 17 determines the impedance of the circuit pathway 13.

A description of the application of impedance sensing for determining minute ventilation would be helpful to determine the scope of relevant variability available for using this invention with different electrode configurations, leads, locations and test pulse characteristics. We recommend review of the book: Clinical Cardiac Pacing, Kenneth Ellenbogen, et al, published by WB Saunders Company, copyright 1995, pages 219–233, incorporated herein by this reference.

Figure 7:
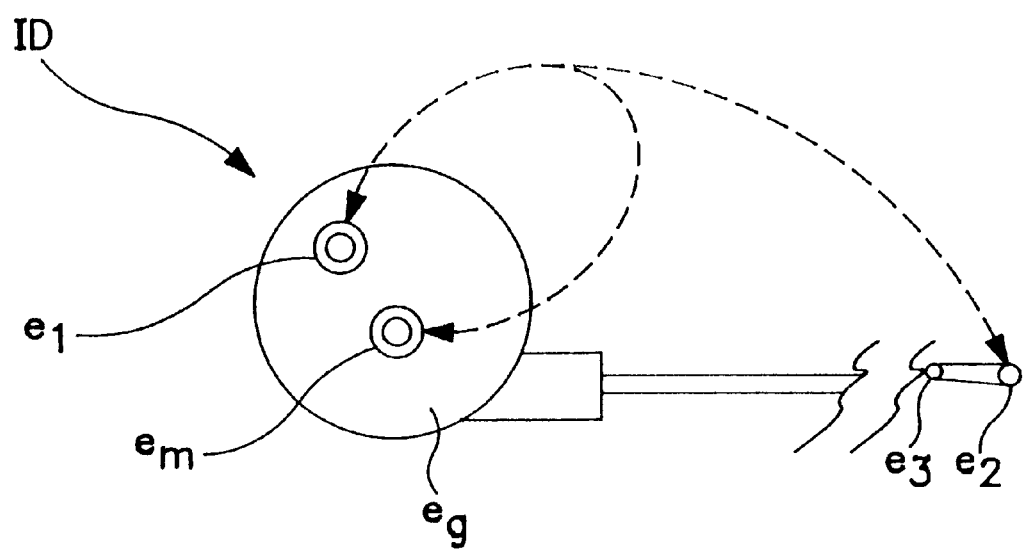
FIG. 7 is a block diagram for device alternatives to FIG. 1.

Because of the possible poor signal characteristics that may be found using the same electrodes for generating the impedance test pulse signal and taking the measurement from the same electrodes, we prefer to measure in a uniform part (or relatively noiseless area) of the field. Both the configuration of electrodes and the values of the test pulses should be programmable. One way to do this is using one electrode, electrically isolated from the large surface indifferent electrode(like the can or housing of a pacemaker, device 10, or other implant) to deliver the test pulse, and a second electrically isolated electrode to measure the voltage difference in the tissue between the indifferent electrode and this second electrode. Another preferred arrangement would use two completely independent electrodes in the field to measure the impedance, thus having a quadripolar system. In various configurations of this invention additional electrodes can be imagined for flexibility where needed or to use electrodes on leads locatable in specific places within the field created by the test (or as we sometimes call it the "excite") pulse. This acceptable variety of configuration to achieve different edema measurement signal values is illustrated in FIG. 7 wherein an implantable device ID has electrodes e1, e2, eg and em and either electrodes e1 or e2 can be used for developing the test pulses. The value being measured (voltage or impedance of the tissue between these electrode pairs) is taken between another electrically isolated measuring electrode em and the indifferent or ground electrode eg; between em and e1; or between em and e2 in the preferred forms. Or, of course, the measurement could be taken between the two test pulse delivery electrodes e1, and eg; or between e2 and eg in the least preferred forms.

As will be described with reference to various figures below, substantial variation can be used for each of the elements described with reference to FIGS. 1 and 2, and still be within the scope of this invention.

Figure 2:
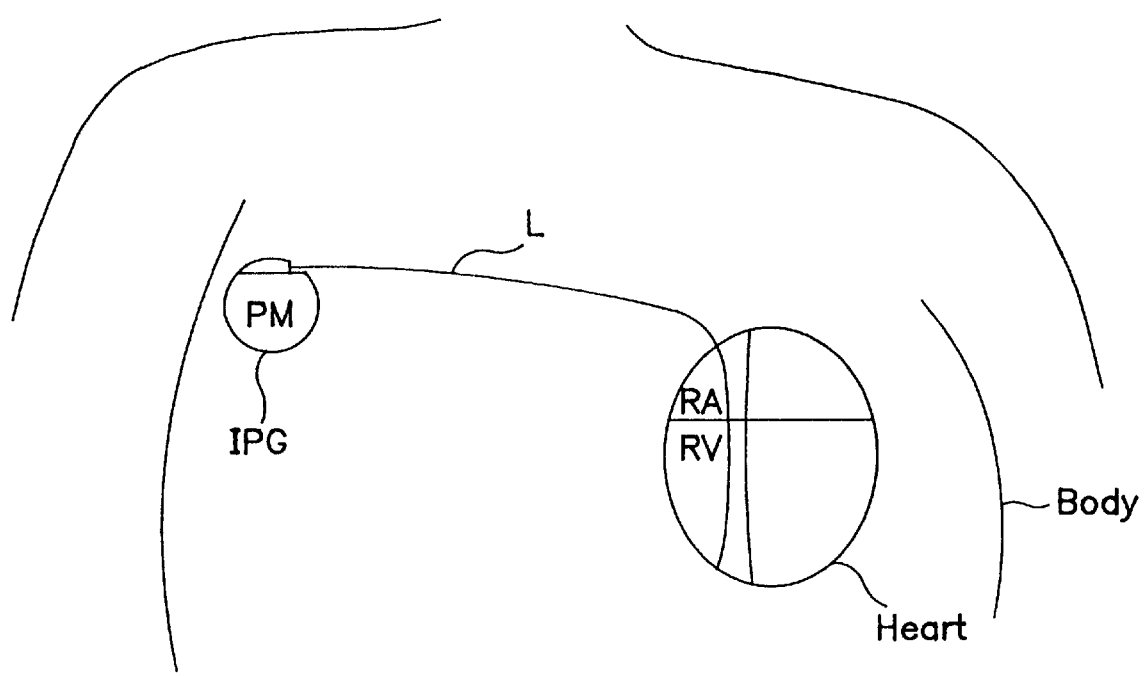
FIG. 2 is a illustration of a common pacemaker device for use with this invention.

In FIG. 2 an alternative apparatus for housing the invention is shown in a body (Body) having a heart. A pacemaker (IPG) is implanted on the right side and has a lead L extending through the Right Atrium (RA) and into the Right Ventricle (RV) of the heart. By using the circuits and teachings of this invention an apparatus such as a pacemaker and lead combination implanted into a living body like that illustrated here can be used to implement this invention. Alternative types of implantable devices may also be used to house this invention including for example, defibrillators, drug infusion devices, spinal cord stimulators or any other implantable device having the minimum external number of electrodes and being provided with an impedance stimulation and measurement circuit.

So as to describe a workable device, a preferred form of the invention is described with reference to FIG. 3, in which a block diagram 30 is included which illustrates the addition of edema monitoring circuit to a dual chamber two lead pacemaker system. In FIG. 4., a block diagram 40 is provided to describe elements useful in finding diagnostically valuable edema signals. For additional beneficial data generation purposes other sensors may be included in the implanted device and data therefrom temporally matched with edema data to provide additionally beneficial diagnostic data. Each sensor can be thought of as a system for providing an indication of patient condition, either when it's output is taken alone or combined in manners known to those in the art to determine patient condition. Such included sensor systems or subsystems could include, for example, diurnal cycle indicators, position or posture indicators, resting indicators, heart beat cycle indicators, breathing indicators, movement indicators, and so forth, each providing a signal value that could be stored or used to trigger an activity of the implanted device.

Figure 3:
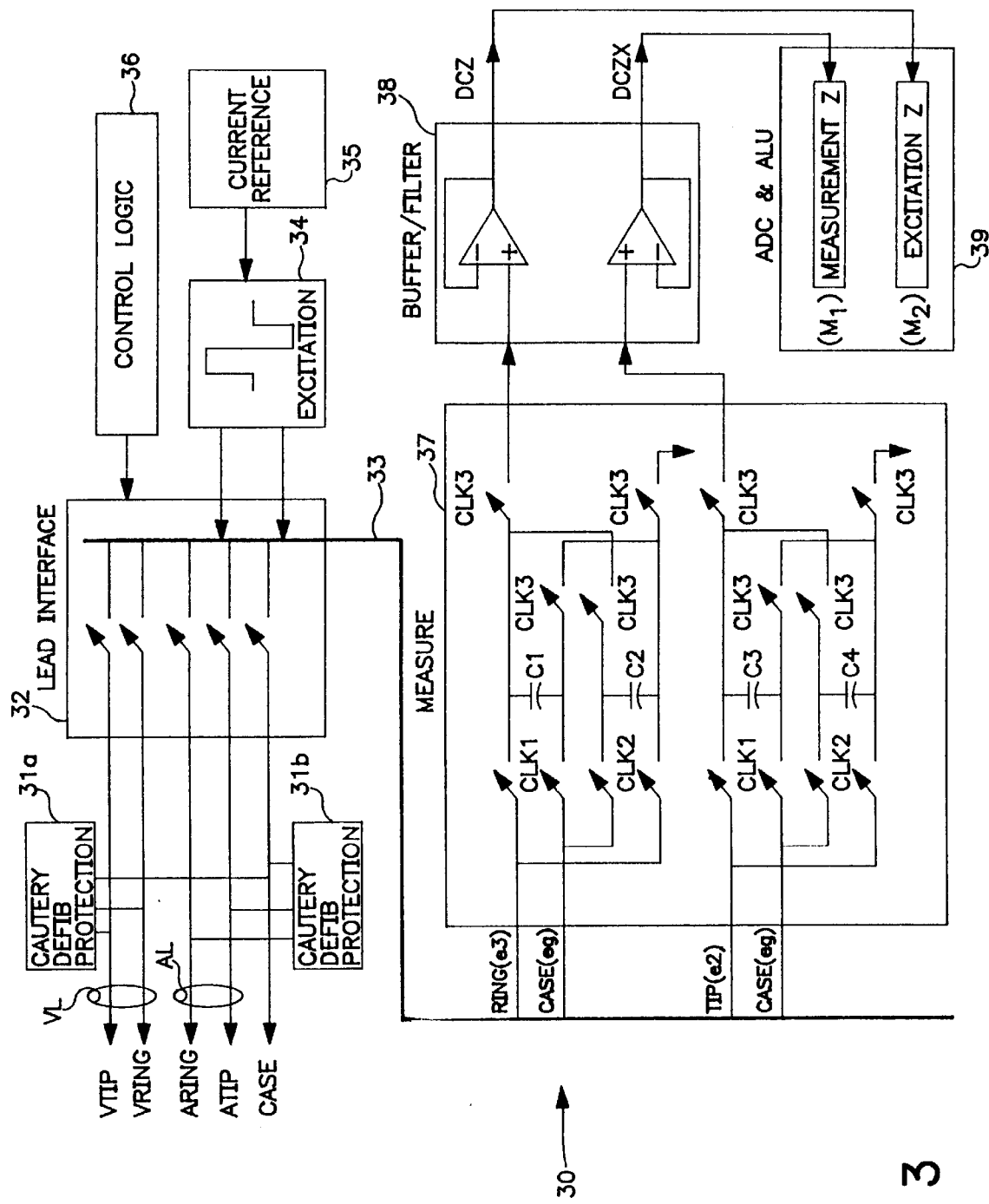
FIG. 3 is a block circuit diagram of a stimulation of a impedance measurement circuit for use with the invention as described herein.
Figure 4:
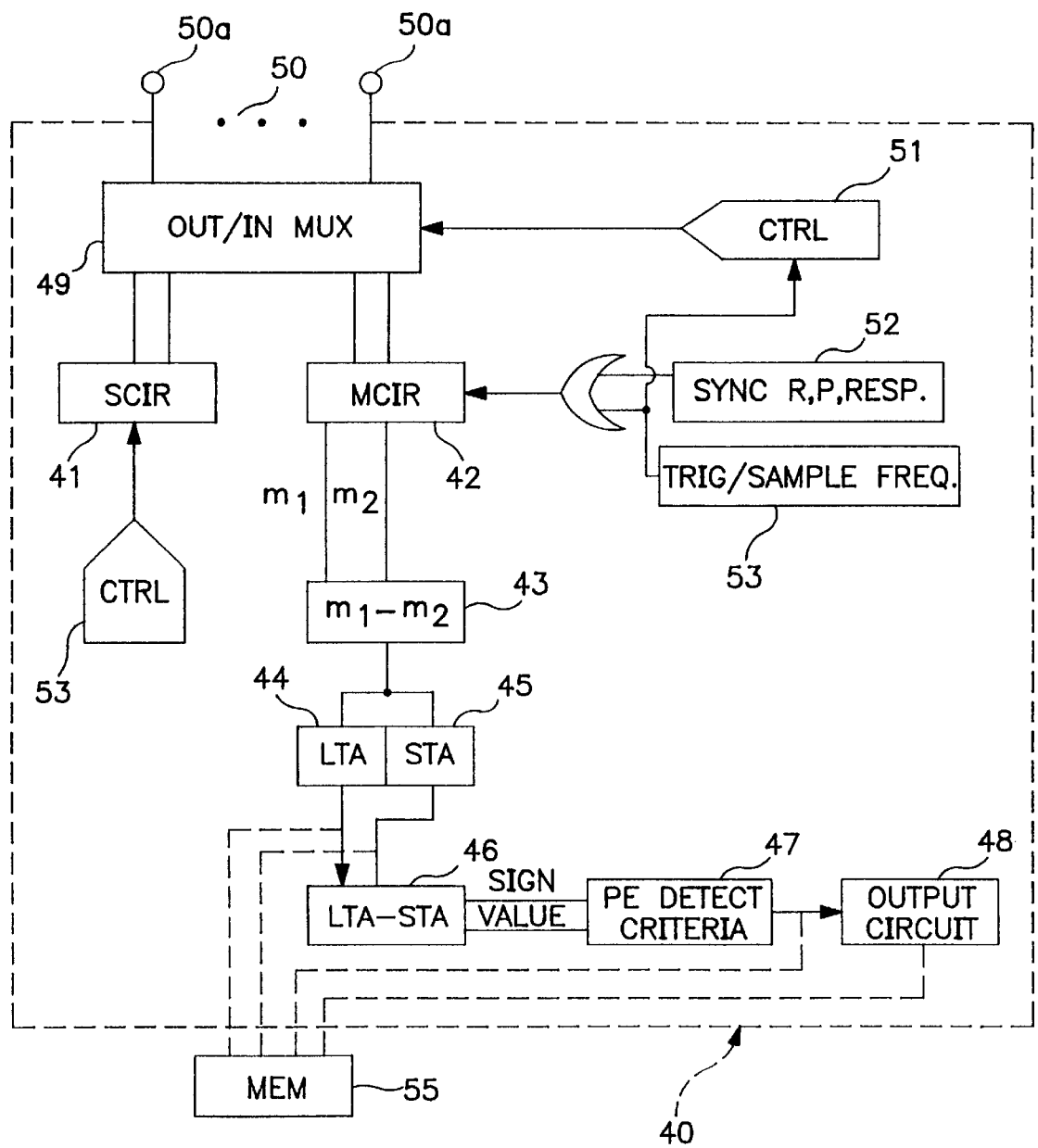
FIG. 4 is a block circuit diagram in accord with a preferred embodiment with this invention.

Referring now to FIG. 3, it will be understood of those by ordinary skill in the art that a ventricular lead VL will have a V tip electrode and a V ring electrode and an atria lead AL will have a A ring and an A tip electrode and that these electrodes are adapted to be inserted into the ventricle and atrium of a patient. A case electrode (or neutral electrode as it may be called) is also provided to the circuit so that measurement may be made between any one of the four electrodes and the case, (or between any two electrodes if it is desired not to measure the impedance between an extended lead electrode and the case). In any device having an electrode in the heart and an electrode located substantially away from the heart such as here with the case electrode in the pacemaker pocket, the kind of transthoracic impedance measurement that will be obtained provides a direct measurement of pulmonary edema.

(We also provide localized edema or impedance measurement (see FIG. 7) in our most preferred embodiments and compare these two values as described with reference to FIG. 4.)

Protection circuits are often provided in implanted devices such as circuits 31A and B in order to protect the more sensitive electronics of the device from electrosurgical cautery in, or defibrillation of, the patient. A lead interface 32 (usually within the pacemaker shell itself and not in the connector block) provides connection between the electrodes and sources of electrical stimulation as well as circuits for measurement. An excitation circuit 34 (usually associated with a current reference circuit 35) and a control logic circuit 36 also supply input to the lead interface 32. As various switching circuits are well know to those of ordinary skill in the art the use of a large scale line 33 (a control bus) to provide electrical connection to the measurement block 37 is shown here to obviate the need to show all possible connections. This block 37 captures the resulting voltage from the excitation provided by circuit 34 and functions as a sample and hold circuit between measurements. The input impedance of this block is preferably very large compared to the excitation and measurement path so as not to affect the result. Preferable values for capacitors C1–C4 are substantially within the ranges of 2pF–50pF based on the current excitation to allow complete charging in an excitation cycle and realization in a integrated circuit design. Measurement circuit 37 is run of course by a clock which in this embodiment has three signals, illustrated in this FIG. and in FIG. 5 as CLK 1, CLK 2, and CLK 3 to time the switches. During CLK 1 the top plate of capacitor C1 is connected to the ring and the bottom plate is connected to the case (the reference). The capacitor C3 top plate is connected to the tip electrode and its bottom plate is connected to the case. This arrangement and timing stores the positive peak voltage on capacitors C1 and C3.

During CLK 2 the top plate of capacitor C2 is connected to the case electrode and the bottom plate is connected to the ring. The capacitor C4 top plate is connected to the case electrode and the bottom plate is connected to the tip electrode. This results in the peak voltage during the negative phase of the excitation being stored on capacitors C2 and C4.

The clock signal phase CLK 3 connects the top plate of capacitors C1 to the top plate of capacitor of C2 with the reference connected to the ground. The top plate of capacitor C3 is also connected to the top plate of capacitor C4. This results in the peak-to-peak excitation voltage on capacitors C1 plus C2 and peak-to-peak measurement voltage on capacitors C3 and C4.

Numerous alternative circuit arrangements are within the skill of the ordinary artisan and could be employed rather than the circuit described here, but it is believed that it will be advantageous to design the circuit with certain constraints. Particularly relevant is having the test pulse delivery occur synchronously to the timing of the impedance measurement. Also depending on the location of the electrodes used for measurement, it is wise to consider synchronization to the heart beat cycle and the respiratory cycles or the variation in measurement resulting from measuring at inconsistent times within these cycles may cause insurmountable difficulties in extracting useful signal from the impedance changes created by these cycles.

For example, using the pacemaker as the vehicle for this invention the transthoracic impedance measurement made between a ring or tip and can electrode pair will vary more during the heart beat cycle than the expected range for significant edema indicative variation in the DC signal. The same will be true to a lesser extent for the breath cycle. If the impedance measurement is taken in some other transthoracic vector, the breath cycle may be a greater influence than the heartbeat cycle on the noise. Where the implant is designed to measure only local edema these heartbeat and breath cycle noise sources will be less of a problem, especially where the device is to be located in an extremity, but one can certainly design in protections to filter out or otherwise obviate these sources. (Exertion and movement noise sources are addressed later in this disclosure).

In one preferred embodiment in which we want to filter out heart beat variation and/or breathing variation from the DC signal, we would employ a buffer filter circuit 38 so as to find both a excitation path baseline impedance, DCZ and a measurement path trans-impedance DCZX. The impedance of DCZ (Z) is equal to (Vring-Vcase)/I ring to case). DCZX impedance is equal to (V tip-V case)/I (ring to case).

Filtering can be implemented in this block as desired. Preferably band pass poles of 0.05 Hz to 0.5 Hz can be realized and we prefer a switched capacitor bandpass filter.

Depending on the device configuration, it may be preferable to convert the voltage values to digital values or to sum the values directly over time to eliminate the cardiac components in the impedance signal as well as other short duration impedance changes. Baseline impedance can be determined by the following equation.

$$Z\ \text{Transthoracic} = \Sigma DCZ + DCZX/2n$$

where n represents an adequate sampling over a extended period. The sampling period in preferred embodiments should be greater than the longest respiration cycle or at five breaths a minute, and the summation period should be at least twelve seconds. A longer period of thirty two to sixty four seconds would further reduce the respiration component in the measurement signal. Impedance measurements can of course be made at sampling intervals appropriate to the device.

In taking a Long Term Average (LTA) signal especially but also for all signals, the potential for super-long term changes should be recognized and compensated for as well. A specific example would be the effect of weight gain on the long term edema signal level, and it's differing effects on trans thoracic measurements and those of local measurements. The differences can be used to algorithmically process and remove or highlight the variance over time in the output data, and can then be used to more accurately asses the amount of tissue edema over the long term changing condition. This additional processing can be done manually or in a computer system outside the patient preferably, but as processing power needs decrease or clear trends in the data become available, it may become feasible to include this kind of processing to the implant itself, allowing for automatic recallibration over the long term and for additional indications of patient health to be monitored.

Figure 5:
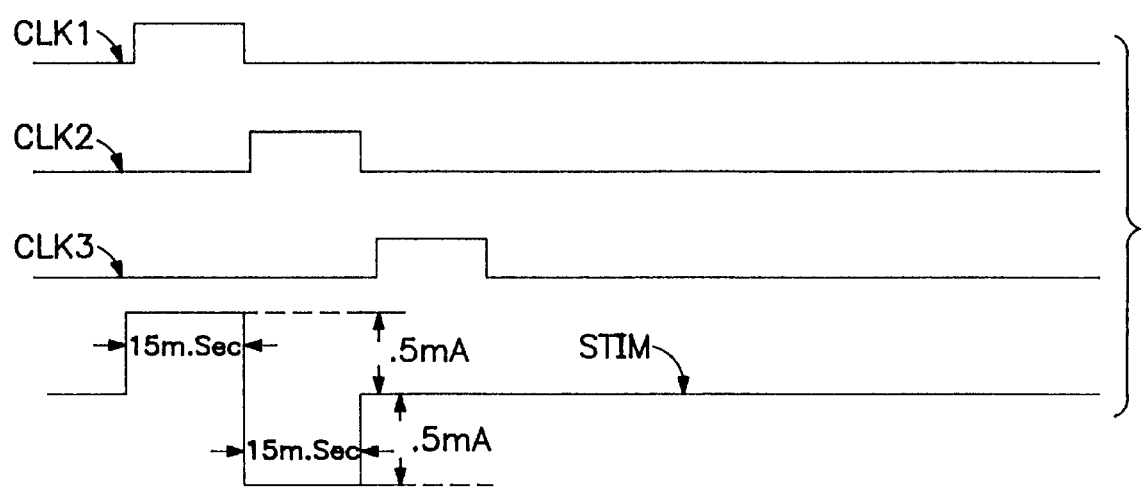
FIG. 5 is a timing diagram for use with this invention.

In FIG. 5, the timing diagram for switching the CLK switches (CLK 1–3) and their timing in relation to the stimulation signal STIM, are shown. It should be recognized that the current (I) ranges from about 1 mA peak-to-peak 10uA peak-to-peak and can be selected depending on the device used for the impedance measurement and other factors which would be apparent to one of ordinary skill in the art. The convenient current reference block 35 of FIG. 3 could be used for this adjustment.

Another preferred way to remove heart and breath cycle noise is to synchronize to the measurement so as to measure only at the same point in the cycles. This is made possible in pacemakers that already use impedance measurements to detect Minute Ventilation (such as can be found in the Kappa 400) pacemakers by Medtronic, or the META DDDR by Telectronics/St. Jude Medical, since they keep track of the breathing cycle and the heart cycle already. By simply adding a trigger signal generator to signal the measurement circuits at a particular value, and then storing the impedance at the time such signal is generated thereby designating it the DC impedance value, the required result is accomplished for that cycle. The trigger signal should preferably coincide with the nearest upcoming preprogrammed measurement time, preferably at 5–15 minute intervals, but anything up to each cycle or every hour would be reasonable. The value could be stored and held so long as it doesn't change. (Many alternatives for filtering are available such as using a sampling rate that corresponds to a factor of one of the cycles and averaging the measurements, for example could be used for one or the other of these cyclic major noise sources.) If the filtered impedance value is seen to change sufficiently(most simply determined by comparing it to the last value accepted for an impedance measurement and determining whether the absolute value of the difference meets a predetermined value minimum), this change criterion can be used to generate a warning or just held for later data retrieval as an additional data point.

If other means or circuits are used to determine a propitious and consistent cycle moment for measurement (other than MV impedance testing pulses and internal cardiac cycle timing values as described generally in the preceding paragraph), such other circuits can be used to trigger a signal in any implanted device. For example, if the device is implanted in a surgically created chest pocket and measures breathing cycles with a motion sensor, strain gauge on a diaphragm, or other activity sensor and uses electrodes to measure a subcutaneous ECG, the output of these sensors can be monitored to determine periodicity of these cycles and exclude measurements made or prevent measurements from being made during inconsistent parts of these cycles. These variations on the inventive concepts taught here are within the ordinary skill of the artisan in this field to implement without undue experimentation now that the invention has been revealed. In the memory and under program control, the device can then respond to the accumulated and processed data to determine appropriate device behavior from a range of preconditioned device behaviors. For example, if the edema level has changed greatly within a short period of time and the pressure values measured confirm that there is a physiologic problem, a drug pump can add diuretic as well as blood pressure medicaments to the patient's body automatically, whereas if the blood pressure has not increased, only the diuretic can be added. These responses could be preprogrammed and modified as an overseeing physician directs.

Referring now to FIG. 4, a circuit block diagram 40 is shown having electrodes 50a–n either situated in leads or located directly on the housing depending on the configuration of the device connected to switching system 49. The circuit 40 has a stimulation circuit 41 and a measurement circuit 42 connected to the electrodes as appropriate by the control circuit 51. (Of course, if only two or three electrodes are used the multiplexor design can be quite simple or reduced to a switch mechanism.)

The measurement circuit 42 is essentially the same circuit illustrated in FIG. 3 (circuit 39) wherein the value of the measurement impedance M1 and the excitation impedance M2 are provided as outputs to a circuit 43 which in FIG. 4's circuit 40 provides a measure of the difference between the two (M1 and M2) to a long term average circuit 44 and short term average 45. Manipulation of the stored values of long term and short term average circuits 44 and 45 which in the preferred embodiments are multiplace register circuits for holding digital values, is accomplished in a comparison circuit or combination circuit 46, which in the preferred embodiment subtracts the short term average value from the long term average value providing as output a sign and absolute value to a physical event detection criteria circuit 47 which in turn provides an output signal to a output circuit 48 which enables the useful application of this value to the patients health.

The measurement circuit 42 is adapted to have input to the preferred embodiment from a synchronization circuit 52 and a trigger and/or sampling frequency circuit 53.

The synchronization circuit can only exist in those preferred embodiments in which the device itself makes a determination of the timing of either respiration, Rwaves, or Pwaves so as to make the sample measurements at the same points in those cycles. A trigger device could be used if desired so that a patient may activate the storage of a event (i.e.), these measurements were made around the time of the activation) at a given time or an attending physician or automatic device may be provided to do so. A sampling frequency circuit can be provided also based on a clocking device within the inventive device such that it determines the time appropriate to take a sample reading.

In all preferred embodiments we would prefer to make measurements during the rest periods of the patient, since this time obviates the need to remove muscle movement and body activity noise sources. Where this is not possible, the addition of activity sensors and common mode rejection of EGM or other signals from the measurements should be employed.

The control circuit 53 is preferably adapted to fire the stimulus circuit so as to deliver a programmable output and pulse width designed to obtain the maximum useful signal. If a circuit like circuit 40 is found in a pacemaker type device and Bipolar leads are used within the Atria and Ventricle, M1 is the value of the Unipolar impedance and M2 is the value of Bipolar impedance. However if a unipolar lead is used, M2's value is zero.

Circuit 47 in the preferred embodiment operates by determining if the sign is positive and the value is greater than a programmable percentage of the long term average (or some other programmable value determined to be appropriate). If this is true, circuit 47 will cause a detection signal to be generated. A memory circuit may be provided to store short term and long term average values as well as data from any of the circuits, other sensor outputs, or output paths. These data may be useful for diagnostic purposes in the patients future.

It will now be apparent that not only a single data point (LTA-STA) can be used to determine the extent and progression of the edema. A chart or history of the impedance (LTA-STA) versus time could be used to determine the effectiveness of drug therapy by including an index circuit or memory circuit with comparative values in the device. A determination of how severe the disease is by how quickly the edema progresses (i.e. if the change was seen over the course of two weeks, versus one day) becomes a measure that has value to the patient and physician and can be a stored value kept in a memory circuit by a device made in keeping with this invention.

With respect to configuration of the electrodes 50, preferred embodiments include four electrodes with one common electrode, three electrode's, and two electrodes. (Reference to other potential electrode configurations was described above at page 6) The determination of pulmonary edema or local edema will be based upon comparison of long term average impedance value compared to the short term average value. A discrimination of pulmonary edema from local edema (or the location of the edema) could be made by comparing the change in the LTA-STA in the local (pocket located) electrodes compared to the change in the LTA-STA in transthoracic electrodes.

The number of samples for long and short term averages are dependent upon the sampling frequency. As we mentioned above it is up to the reader to chose a preferred sampling rate, but examples of sampling rates having some usefulness would include 5 minutes, 15 minutes, 1 hour, 2 hours, 1 day, and so forth. It depends on the capacity of the device battery to continue to make measurements and the period of time prefered to monitor that the selection of periodicity is based on. If it is sufficient to sample only when the patient is asleep, once a day may be enough. Long term average preferably represents the number of days (in the most preferred embodiment three to thirty) while the short term average represents the number of hours (preferably one to forty-eight). However, if the device is expected to detect very short term rises in impedance, a short term value should be measured in minutes and long term in less than a week. This kind of measurement timing setup would accommodate the rapid rise that sometimes hospitalizes patients after eating a salty meal, for example, allowing a warning to be generated or direct intervention started without the need for hospitalization. When the difference between the average signal value of the long term average storage circuit verses the value in the short term average storage circuit reaches a critical level (which should be programmable for the particular patient and adaptable during implant), a determination is made that the edema is problematic. Other circuits or processes could be used to make this kind of discrimination to avoid noise, whether cyclic or transient. In general these can be referred to as noise discrimination circuit processes since they may require use of data processing techniques or analog circuitry or both to implement the noise reduction plan. Both types of design are known to those of skill in this art and suggestions for preferred forms have been suggested already.

It is worth mentioning for completeness that any of the data stored in the device memory is read out by telemetry preferably. Many types of communication with implanted devices is known including telemetry from the pacemaker art, including U.S. Pat. No. 5,354,319, issued to Wyborny or U.S. Pat. Nos. 5,324 315 and 5,292,343 and 5,117,825 issued to Grevious et al, amongst many others. For example, the U.S. Pat. No. 4,987,897 issued to Funke describes a communications system that uses the body as a transmissions medium. Since many are known and available, it is therefore sufficient to state that any means or apparatus system could be used to read out data collected by a device such as the ones described herein without deviating from the intent of this inventive teaching. We prefer the standard pacemaker telemetry approaches for our preferred embodiments but only because they are the most familiar. The patents cited by this paragraph are incorporated by this reference in their entirety.

It should also be noted that a patient trigger or activator can be used by a communications apparatus in conformity with the last paragraph to which a button or other patient manipulable device is attached to signal the implant to begin data readout, store a more complete form of data representing perhaps more measurements per unit time after the trigger is activated, and so forth. This kind of device could also be employed to enhance transtelephonic communication with a medical care provider if it only additionally included apparatus to connect the activator to the telephonic network.

Figure 6:
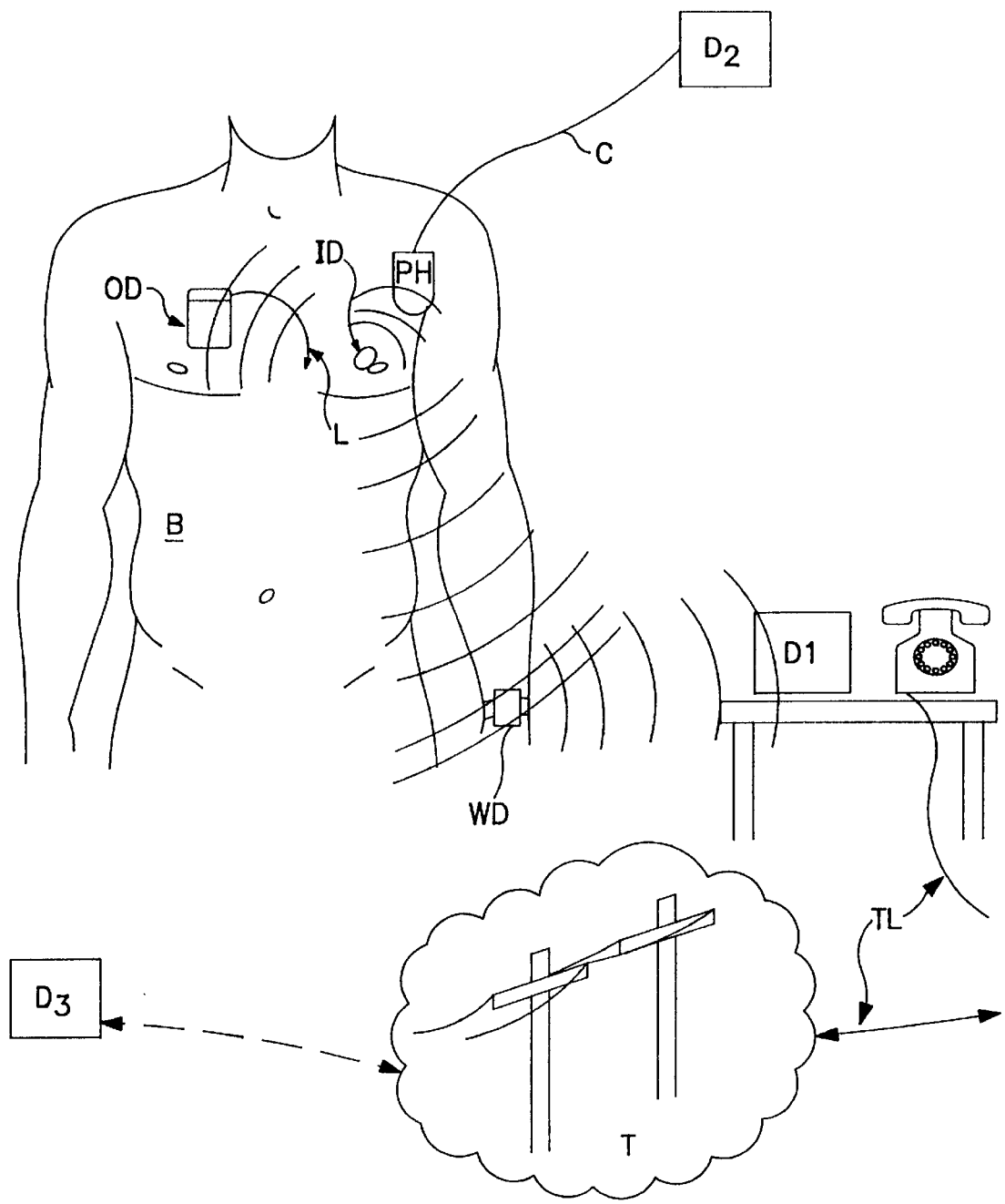
FIG. 6 is a heuristic block diagram of a body, implanted devices and communication systems useful with this invention.

Such a device could advantageously be like the device WD in FIG. 6. It would merely require a handy user interface like a button, switch or knob and perhaps lights to acknowledge the trigger and so forth. Alternatively by tapping on the body in the vicinity of the device or holding a magnet over it or some other activation scheme known in the art may be used.

Additional triggers for storing data on measurements made at the time of a trigger signal could be automatic, based on regular measurements made by the implanted device. For example, if a doctor believes a 10% change in LTA over a two week period should invoke hospitalization, he could set such a trigger in the implanted device memory. The device then would incorporate an automatic process for checking the data against the automatic trigger values, and when the comparison indicated a trigger condition, cause activation of either a readout, or an alarm or a change in the type of measured data stored, depending on how the device were programmed. Alternatively, of course, this automatic trigger could be located in the external device that reads out the data from the implant. This would be preferable in most situations since the external device need not be as power constrained as the implant. Thus it could process the data more cheaply for a determination of whether the automatic trigger values have been reached. There are, of course many kinds of automatic rigger mechanisms that can be used, including the reaching of an absolute measurement value, pattern matching with an overall change in values plus reference to an absolute value in a limited time, absolute change between the LTA and STA values and so forth. Any of these can be factory set or set by physicians/attendants in the field, and if transtelephonic communications are used, from remote locations.

Trend data retrieved from the implant's memory can be used to chart the variation over time between the two values (LTA and STA) or any other stored values, which could be used to enhance the diagnostic value of the data for the physician.

Refer now to FIGS. 8 and 9 in which the more generalized forms of the invention are illustrated, a block diagram 80 having a similar input/output setup to circuit 40 of FIG. 4, such that the impedance stimulus pulses and measurements may be gathered through the same electrode system, that is, in FIG. 8, electrodes 81a–n and multiplexor or switching circuit 82. In this more generalized device, a bus or set of connections transports digital signals between functional elements of the device including the microcontroller or processor 87/86, respectively, a memory 88, the impedance stimulus circuit 83, the impedance measurement circuit 85 and the other sensor circuits 89. With these parts a device can have the controller 87/86 schedule the delivery of any stimulation pulses needed and their intensity to each of the sensor systems 89a or 89 when such stimulus is required and allow for the transport of measured data from such systems, as needed also. A control and storage mechanism may be a unitary memory or a plurality of memories here illustrated as memory 88. The controller would allow sensor data to be routed to memory for storage and later communication to the world outside the implantable device through a telemetry subsystem 99. One of ordinary skill in the art is familiar with how to employ such components to build a system as described. In fact, some variation can be easily introduced, such as having all sensor subsystems communicate analog data to a single analog to digital converter(not shown). The way it is illustrated in FIG. 8 A/D conversion and it's converse are made part of the sensor subsystems as illustrated in the edema measurement subsystem 89a by having A/D and D/A circuits in the measurement and stimulus circuits.

For convenient reference the kind of data available from sensor subsystems (89) would be ECG data, marker channel data, other device state data, pressure, pedal impacts, activity, body position, temperature, heart rate, (or when compiled over time) heart rate variability, heart events (fibrillation or tachyarrhythmia episodes and their frequency and duration), respiration, blood oxygen levels, patient symptoms monitor triggered measurements due to patient activation by a patient monitor activator (which could be a part of device WD in FIG. 6, for example) as well as the described in detail pulmonary or transthoracic edema and local edema related impedance values or any other sensor subsystems and combinations thereof that are now available. It is even possible to use the inventive concepts described herein for these other sensor subsystems without edema if desired.

FIG. 9 illustrates the general flow 90 of progress in developing diagnostic data from each of the sensor subsystems and can be incorporated into highly complex algorithms for multiple subsystems and for coordinating the storage and measurement of all sensor data. Beginning with the data gathering stage, if a stimulus pulse is required it is given and the measurement is made 91. No stimulus pulse would be required for example is an activity sensor that was self reporting. These values are stored in the device memory 92, and then acted upon according to a program or circuit 93 that locates the measurement values in relation to or with respect to time and other sensor measurements. This program can have branches to alarms or initiation routines to change the behavior of an implanted device based on the values stored at this stage if desired. In this stage also, calibration against stored reference values or setting up on new reference values is handled.

If changes are required, say for example in the level of stimulus required to elicit useful sensor response, they are determined at the next step 94. Such changes in the value of the stimulus test pulses can be due to customization needs for a particular patient, to optimize the Signal-to Noise Ratio(SNR), to prevent accidental or unwanted local muscle stimulation, etc. Alternatively, the excitation and measurement paths (which electrodes are selected for stimulus and measurement) should be switchable to determine the location of the edema and as part of the algorithm for detecting changes in edema, or simply to improve the SNR. The program will then execute these changes, wait for the next appropriate time to take a measurement from this sensor subsystem and return to step 91.

FIG. 6 illustrates a patient body B having an implanted device in accord with the invention ID for determining a value of impedance indicative of edema. For example purposes also illustrated another implantable device OD, as illustrated here, a pacemaker having a lead L.

In the clinical setting the doctor will use a programmer device which is either a hand held unit like the PH unit which is held in proximity to the body B or a hand held device associated with a larger "programmer" which in common use is similar in power to a personal computer running an Intel 80486 or Pentium processor. This unit is illustrated heuristically here with the numeral D2, connected to the telemetry containing head PH by a connector cord C. Substantial diagnostic testing and processing can be done, giving the patient stress testing, drug treatments, and so forth with the doctor in attendance since the immediate data from the implant can be accessed and used by the physician to test the body's physiologic responses to various test conditions. Various configurations of D2 and PH with respect to telemetric communications to implants are well known and any such systems could be exploited for this invention. The new data now available from the implanted inventive device ID enhances this physician function by providing an edema and edema history signal containing data about the changes in the edema parameter over time to the physician. This data can be processed with data from other implanted sensors which may be distributed between the implanted devices OD and ID, etc., or all from one device, such as a pacemaker like device OD. It is already known in the art to have and use implantable sensors to monitor and record data including activity sensed, heart rate, heart rate variability, respiration, minute ventilation and variability of, arrhythmia frequency and duration, averages of these values over long term, pressure at various sensor locations, O2 saturation at various sensor locations, time located patient activated data records for holding various pieces of these data sets around a temporal marker set by a patient activated signaling device (which could be incorporated into a device such as WD, or some other convenient unit) for diagnosing patient symptoms, and so on. However, the use of an impedance sensor dedicated to generate data specific to edema conditions and history has not heretofore been seen. Combining these edema measurements with any of these other signal data provides an enhanced diagnostic and patient management efficacy to all the devices that can be used in the FIG. 6 environments. For example, the ID device could contain a looping memory activated by trigger signals sent either through a patient activator (which advantageously can be located in device WD) or by physiologic signals generated by one of the sensor systems (systems 89 or 89a of FIG. 8).

Continuing to refer to FIG. 6, the inventive implantable device ID can also be used in settings remote from direct physician contact to further its usefulness. A wearable device WD can be used to extend the communications range without substantially increasing battery usage by the implant ID for sending communication signals. A patent illustrating this concept is U.S. Pat. No. 5,113,869 showing that a wearable device could be used in such a manner. As power considerations change and communication to implants becomes less costly, it is feasible to eliminate an intermediate device such as WD, but for the foreseeable future such devices are expected to be used for transtelephonic communications with implants. A home monitor device such as D1 may be kept in a location within range of the communications capabilities of the device WD and connect to a telephone line TL system to a telephony or communications network T (which may be worldwide in scope) or through other communications channels not shown to reach a device D3 that is located at a physician station, hospital or clinic and which can perform the same functions described for the programmer device (D2) above.

Preferably, device D3 can also communicate through the telephone or radio frequency channel to the wearable device WD. In this way too, this communicated information could be used to modify the functioning of the implanted devices, OD and/or ID. These changes could be modification to data collection methods, type of data collected or trigger release values for drug or stimulation therapies.

In some preferred embodiment devices we would use the respiratory rate as an indicator of edema or lung water. This can be monitored long term like the DC impedance signal, but instead of filtering out the respiration signals as noise, we would for these devices use the respiration varied impedance measures to determine breath rate. It is well known how to do this. Medtronic produced two pacemakers, the Legend Plus series and the Kappa 400 more recently that measure minute ventilation, which requires a determination of a breathing rate to provide a rate response function. Another called the RDP3 or MB-1 was reported in "Rate responsive Pacing with a Pacemaker that detects respiratory rate (Biorate); Clinical advantages and complications," by Lau et al, CLINICAL CARDIOLOGY, May, 1988, 11(5) p318–24, ISSN 0160=9289, Therefore it can readily be seen that determining respiration rate is not outside the skill of those of ordinary skill in this art. In our device we use the signals described above for counting breaths. An equation representative of how this function works is Respiratory Rate=Minute Ventilation divided by TV, where TV is the maximum value of DCZ.

It is up to the designer of the device, of course, but alternative methods are available to generate a reliable respiration rate signal; for another example see Plicchi and Canducci, U.S. Pat. No. 4,576,183. All that is required is that a reasonably reliable count of respiration per unit time be maintained and reviewed on an ongoing basis to determine the change vector. A single memory element could be used to record whether each sample is moving up or down in rate if desired, but we prefer to keep some value taken at several measurement so that the data can be relayed to a doctor for careful analysis.

It is expected that measurement over sleep periods, with reduced muscle movement artifacts will yield a cleaner signal, so we prefer using an additional trigger to time the measurements to occur during the patient's sleep cycle. A choice of a suitable sleep trigger is up to the designer, but it could be done in a number of ways such as waiting(perhaps based on a timer and a timeout period) for a period of, say, 15 minutes in which no noise artifacts show up in the signal, timing the sampling periods to correspond with the patient sleep times using a 24 hour clock in the device, and so forth. Many other devices and methods for determining sleep periods are known and may be applied here if desired.

A uniquely valuable enhancement would be the addition of an algorithm to detect Cheyne-Stokes respiration which often is present during sleep as a well known indicator of fluid build-up. By simply monitoring for rapid respiration rates and then closely observing the respiration signal after short episodes of rapid rates, one can easily generate a marker in memory to indicate that such an episode has occurred when shallow breathing or absence of breathing is detected after bursts of high respiration rate.

To exclude from consideration for edema monitoring those rises in respiration rate that occur because of patient exercise or other activity, we use an activity sensor like the activity crystal sensors or accelerometers commonly used for activity measurement in modern pacemakers to generate a signal indicative of patient activity level. If the level respiration rises only during or after periods of indicated increased patient activity, the value of a signal based on respiration rate should be decreased. The respiratory rate taken during periods of no activity is preferred to measure long-term breathing rate trends. In the preferred embodiment we use a Respiratory Rate/Activity or Accelerometer Parameter coefficient that is calculated on a daily basis. Thus two independent values are generated. One value is generated for activity and a value is generated for respiration rate and the ratio of these two is monitored. A change in this ratio causes an increase in the value used to indicate a troubling rise in edema. In other words, the change may indicate more or less breathing during exertion, thus indicating an improvement or deterioration in lung fluid levels.

A device can be constructed using the respiration rate as described alone or in combination with the DC impedance measurement of edema described above. If both are used a mixed value should ultimately be relied upon to indicate the level of edema the patient is subjected to. Many ways can be devised to combine these signals, including simply adding them throughout the potential range and using the total value for the indicator; relying on one measure only, in situations where it is superior, or simply recording both separately and reporting them out through telemetry for analysis together by a doctor or other attendant (human or automatic). Alarms can be initiated thorough whatever patient or doctor communication system is used with the device at whatever level is programmed in for the variable or variables used to evaluate these measures of edema.

In our most preferred embodiment, we would use a combination of breathing rate rise over 10% per 24 hour period with or without any indication of DC impedance measurement as sufficient to generate an alarm. Likewise a 20% rise in edema measured by DC filtered signal value should suffice to generate an edema alert alarm. Finally the presence of a newly discovered Chyene-Stokes episode or, if expected, perhaps the appearance of two Cheyne-Stokes episodes in one 24 hour period or one with either of the other just mentioned edema signal value percentage changes should be sufficient to generate the alarm.

In situations where the device is communicating with or a part of a therapy delivery device, response to edema levels, however measured may be used to trigger or adapt therapies, in any situation described above with reference to the alarm.

Figure 10:
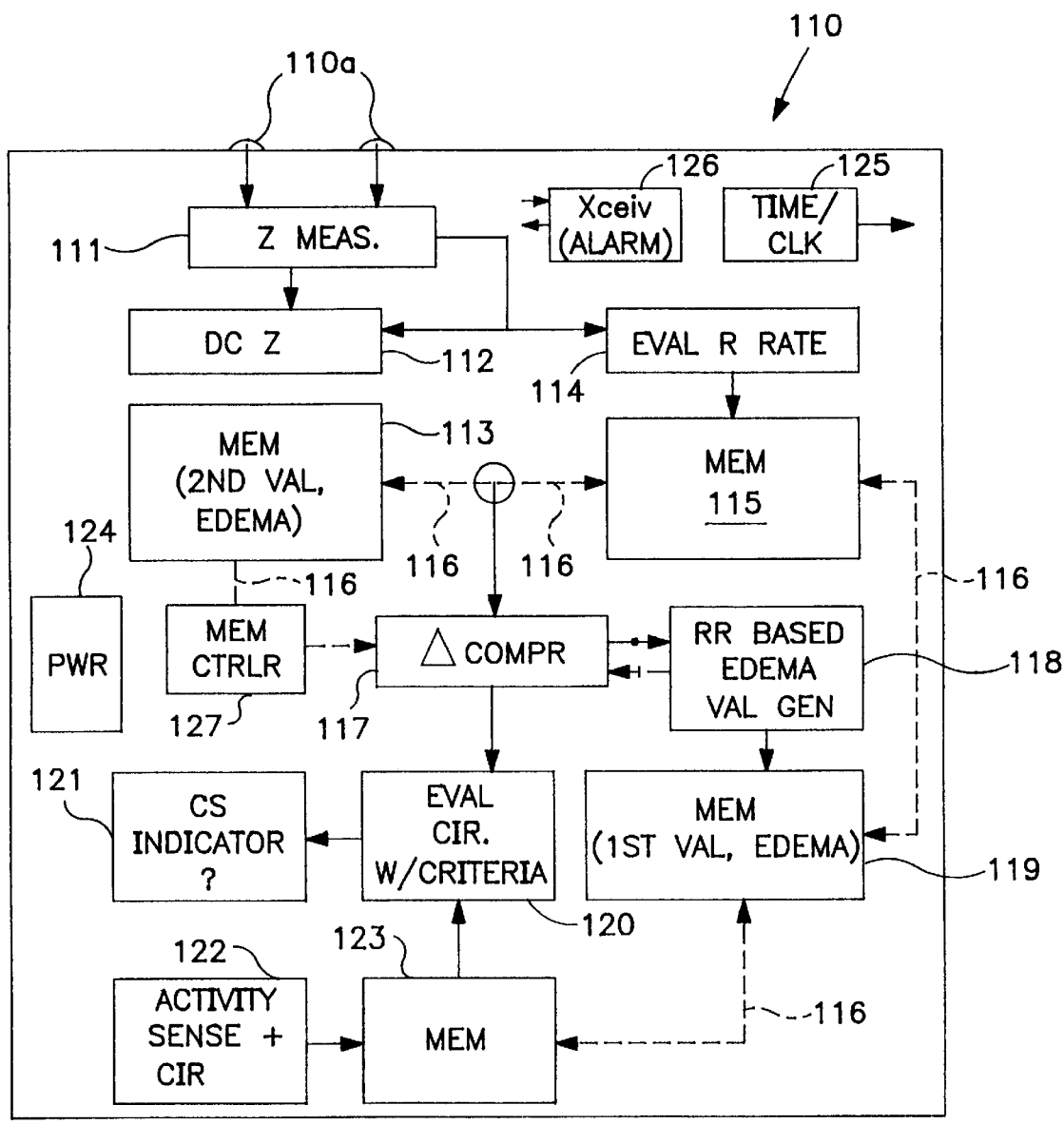
FIG. 10 is a block diagram of a device in accord with the invention.

In FIG. 10, an idealized implantable device 110 is illustrated heuristically with a body compatible shell 110b (which could of course be composed of Titanium or ceramic, or any other body compatible material suitable for housing an implant in a living body) surrounding its component circuits 111–124 and any others desired (but not shown here) by the designer of the device 110 to supplement the inventive circuitry arrangement described herein. For evaluation of impedance measurements to derive a respiratory rate signal one requires an impedance measurement circuit 111 connected to an electrode means on the shell or a lead or similar appendage attached to the shell (here illustrated as two bumps 110a) and a circuit to evaluate changes in the value of the impedance measurements over time. As is well known in the art (and mentioned above implemented in present pacemakers), The impedance measurement can find a value for a respiratory rate signal from counting breaths represented by an approximation of a sinusoidal variation in the impedance occurring within the potential range of breathing rates. In FIG. 10, this determination of respiration rate occurs in the circuit 114. It should be understood that this ability to determine breathing rate is known in the art through at least the methods described in U.S. Pat. No. 4,576,183 (Plicchi and Canducci) and 5,271,395 (Wahlstrand et al.). Generally in block 114 a circuit should provide conversion of an AC impedance signal from the change in impedance tot a respiration rate through bandpass filtering, zero-crossing detection, and if desired, template matching of the digitized waveform. Any design that gives a fairly accurate assessment of respiration rate is acceptable, however.

For completeness(in some embodiments), a DC value of Z may be maintained to take advantage of the potential for determining edema directly from the changes in the impedance signal as described above, and this function occurs in FIG. 10 in circuit 112.

A memory circuit is provided in device 110 which herein is illustrated as being in 4 potential parts, memory circuits 113, 115, 119 and 123. Of course the designer may subdivide or consolidate a memory circuit in any way desired and this is indicated in FIG. 10 by the dotted line 116, suggesting by way of illustration that the configuration of the memory circuitry is best left to the final designer of a particular implementation of this invention.

A timing or clock circuit 125 should be provided to coordinate the storage of data related to each evaluation so that histories of such data can be maintained. As illustrated here, the DC impedance is stored as a secondary or second value set of edema values in memory 113, the respiratory rate values in memory 115 and the respiratory rate change that indicates an edema value (here a primary or first edema value)is stored in memory 119.

An alternate and independent activity sensor and associated signal value generation circuit 122(any known kind could be used) may be provided for a preferred embodiment. This activity sensor and value generator can have its own historical values stored in a piece of memory too, here memory 123.

At any time desired in accord with the needs of the preferred design, the current value of any one of the stored values can be compared to a current or past value of either the same the same or any other one of the stored values. This means that the change in rate, as found in circuit 117 can be used to evaluate the respiration rate, and that the respiration rate can be compared. If desired a memory controller 127 can coordinate these evaluations according to a program that may also be in software stored in the memory, but currently in preferred designs hardwired circuitry (not shown) cycles through comparisons required by the particular design. In this way the illustrated flexibility is compromised for cost reasons. The comparitor circuit 117 output should be qualified by an evaluation circuit 120, preferably each time a comparison is made to determine if the results of that comparison indicate a need to generate other signals that trigger an alarm or a readout or a therapy, depending on the configuration of the device. For example, if the respiratory rate has risen very quickly (thus meeting a criteria stored in or accessible to circuit 120, a signal should be sent to the Cheyne Stokes indicator circuit 121 to see if the change should generate an alarm. If circuit 121 determines that it is appropriate it should send a signal to the transceiver circuit 126 to perform its function suitable to receiving a signal from said CS indicator circuit 121. Circuit 126 may be a circuit to transmit data through telemetry to a device adapted to receive such telemetered data outside the body as illustrated in earlier Figs., or it could be a simple alarm that vibrates or generates a sound from within the patient. It can be triggered by the evaluation circuit any time appropriate criteria are met by the output of the comparitor circuit 117, all of which are described above. Additionally circuit 126 may readout the memory contents or parts thereof on receiving an inquiry signal from an external device, or automatically telemeter out data based on an the expiry of a timer or other signal generated by clock circuit 125.

As with any implanted device there should be a source of power, here illustrated as power supply 124, which of course could be a battery or power generator of any kind suitable for powering implanted devices, so as to supply power to the circuits used in the device and to generate pulses for impedance measurement.

Figure 11:
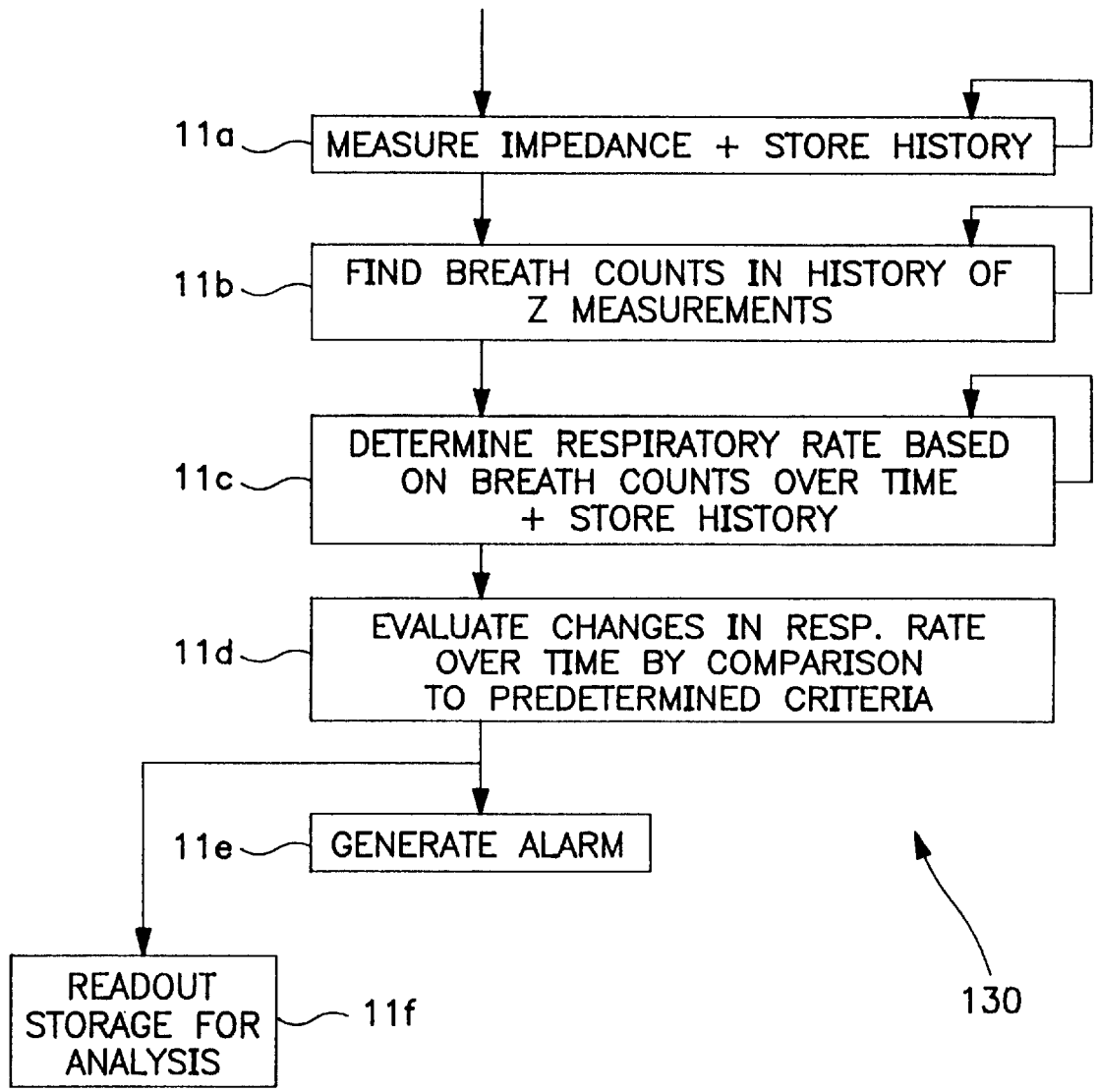
FIG. 11 is a flow diagram illustrating steps for evaluating edema using respiratory rate.

In FIG. 11 a flow diagram 130 illustrates a method for using the measure of respiratory rate over time to generate an evaluation of edema or lung water. It is assumed that he impedance measures are made in the thoracic region of the body by an implanted device as described above.

Step 11a measures the impedance and stores the history, repeating itself continuously as indicated by the curved arrow. In Step 11b, each breath count is determined by review of the history of impedance measurements. A rate is then determined and stored as a current in Step 11c. On their own appropriate cycle times, as would be apparent to one of skill in this art, both steps 11b and 11c iterate and store their determined values as history. As can easily be appreciated, the past history of a prior step may be ignored once a new datapoint is generated by a later step if the only data desired is that determined in the later step. Thus history memory circuitry can be conserved.

In Step 11d, the history of respiratory rate from 11c is evaluated. Here a determination is made as to whether it is tending faster or slower and whether it meets preestablished criteria to proceed to step 11e and to generate an alarm. If the device in which this method is used does more than generate an alarm, it should readout the storage for analysis by a health professional, Step 11f. The preestablished criteria can be stored in the device during manufacture or may be set and reset by an attending physician depending on patient conditions. They may, of course, be comparative criteria indicating simply a vector of edema measurements or may be combined with other physiologic indicators as described above to establish more complex or more reliable criteria.

An easy way to turn the data into diagnostically useful data is to store a respiratory rate to activity level parameter history longitudinally over time. Then an edema level indicator circuit can generate a signal value representative of whether edema or lung water is worsening or improving, based on evaluation of said parameter history. The doctor can simply look at the change in this value over time to assist in his care of the patient. This could be called simply a measure of patient health, rather than edema since respiratory rate may correspond to other simultaneously occurring changes in patient physiologic condition.

The invention as described and illustrated herein is only limited by the following appended claims.

What is claimed is:

1. Implantable apparatus for detection of impedance measurement in a region of a living body's tissue, having a plurality of electrodes exposed to said body tissue on an outer surface of a housing or on another support coupled to said body, said housing containing electrical energy pulse delivery means connected to at least one of said plurality of electrodes so as to create an electric field in said body in an area of tissue around and adjacent said one electrode and energy measurement means connected to at least one other of said plurality of said electrodes also located within said electric field, so that impedance measurements in the living body can be made in said field, said implantable device further characterized by having:

timing circuit for timing the measurement of impedance to coincide with delivery of said energy pulse, memory circuit for storing a value representative of a dc value of said measured impedance at an instant in time, dc sampling offset circuit for determining a dc offset value of a next measurement of said impedance and connected to provide a dc offset value signal to said memory circuit, edema valuation and output circuit for generating output signals indicative of a level of edema related to the impedance values from in said memory circuit and said offset circuit, and wherein said memory circuit stores either said dc offset values or said dc values or both, over a period of days.

2. An implantable apparatus as set forth in claim 1 and having circuit process for discriminating impedance noise signals generatable by said living body's heart pumping and breathing cycles so as to remove cyclic noise such body activities would otherwise introduce into said impedance measurement signals.

3. An implantable device as set forth in claim 1 and having a circuit process for discriminating impedance noise signals generatable by said living body's electromyographic and motion signals so as to remove the noise such body activities would otherwise introduce into said impedance measurement signals.

4. An implantable device as set forth in claim 3 wherein said noise discriminating circuit process comprises a rest cycle determining timing circuit means for generating a timing signal to limit impedance measurements to times that the body is determined by said rest cycle timing and determining circuit means to be at rest.

5. An implantable apparatus as set forth in claim 1 and further comprising a comparitor and trigger circuit means for determining significant events based on a comparison of relative values of the stored impedance value signals to predetermined trigger values.

6. An implantable apparatus as set forth in claim 1 wherein an additional physiologic indicator value is measured by another sensor circuit and said other physiologic value is employed with said edema value to determine appropriate device behavior from a range of preconditioned device behaviors.

7. An implantable apparatus as set forth in claim 1 wherein said memory means stores data related to significant events and history of impedance measurements.

8. An implantable apparatus as set forth in claim 1 and having power generator means for continuous long term operation of said device.

9. An implantable apparatus as set forth in claim 1, where said electric energy pulse delivery means is adjustable to produce programmable output values of impedance pulses.

10. An implantable apparatus as set forth in claim 1 and wherein the impedance measurement is switchable between more than two electrodes to obtain best position for signal to noise.

11. An implantable apparatus as set forth in claim 1 and having timing means or timing means and sensing means to provide synchronizing output pulses to physiologically recurring signals indicative of body cycles and conditions including:

diurnal cycle indicators, position indicators, posture indicators, resting indicators, heart beat cycle indicators, breathing indicators, or movement indicators.

12. An implantable apparatus as set forth in claim 1 having additional impedance circuit electrodes, at least one of which is adapted to be located in an appendage or near the heart.

13. An implantable apparatus as set forth in claim 1 wherein said device housing additionally houses or communicates with an implanted device of the kind listed: Pacemaker, Implantable Defibrillator, Drug pump, Loop ECG recorder, hemodynamic paramater recorder/monitor.

14. Implantable apparatus for detection of impedance measurement in a region of a living body's tissue, having a plurality of electrodes exposed to said body tissue on an outer surface of a housing or on another support coupled to said body, said housing containing electrical energy pulse delivery means connected to at least one of said plurality of electrodes so as to create an electric field in said body in an area of tissue around and adjacent said one electrode and energy measurement means connected to at least one other of said plurality of said electrodes also located within said electric field, so that impedance measurements in the living body can be made in said field, said implantable device further characterized by having:

timing circuit for timing the measurement of impedance to coincide with delivery of said energy pulse, memory circuit for storing a value representative of a dc value of said measured impedance at an instant in time, dc sampling offset circuit for determining a dc offset value of a next measurement of said impedance and connected to provide a dc offset value signal to said memory circuit, edema valuation and output circuit for generating output signals indicative of a level of edema related to the impedance values from in said memory circuit and said offset circuit, wherein said edema valuation and output circuit for generating comprises LTA/STA determining circuit means wherein a processor circuit derives a LTA signal value and a STA signal value based on the values of impedance stored over a predefined long term and short term, respectively for determining an LTA value and an STA value and memory means for storing said determined LTA and STA values and LTA/STA updating circuit means for updating said STA and LTA values based on new measurements of impedance.

15. An implantable device for chronic implant into a living body having at least one lead adapted for location in the heart of said body and means for generating electrical output pulses between said at least one lead and another electrode so as to enable the measurement of impedance between said at least one lead and said other electrode, the improvement comprising a impedance determination means to determine the impedance of the thoracic cavity of the body based on the dc value of impedance measured between said lead and said electrode, edema evaluation means to determine values representing a level of edema based on said measurement at times over a course of days, and means for storing said value representing a level of impedance in said device for said times over said course of days.

16. An implantable device as set forth in claim 15 and having circuit process for discriminating impedance noise signals generatable by said living body's heart pumping and breathing cycles so as to remove cyclic noise such body activities would otherwise introduce into said impedance measurement signals.

17. An implantable device as set forth in claim 15 and having a circuit process for discriminating impedance noise signals generatable by said living body's electromyographic and motion signals so as to remove the noise such body activities would otherwise introduce into said impedance measurement signals.

18. An implantable device as set forth in claim 17 wherein said noise discriminating circuit process comprises a rest cycle determining timing circuit means for generating a timing signal to limit impedance measurements to times that the body is determined by said rest cycle timing and determining circuit means to be at rest.

19. An implantable device as set forth in claim 15 and further comprising a comparitor and trigger circuit means for determining significant events based on a comparison of relative values of the stored impedance value signals to predetermined trigger values.

20. An implantable device as set forth in claim 15 wherein an additional physiologic indicator value is measured by another sensor circuit and said other physiologic value is employed with said edema value to determine appropriate device behavior from a range of preconditioned device behaviors.

21. An implantable device as set forth in claims 15 wherein said memory means stores data related to significant events and history of impedance measurements.

22. An implantable device as set forth in claim 15 and having power generator means for continuous long term operation of said device.

23. An implantable apparatus as set forth in claim 1, where said means for generating electrical output pulses is adjustable to produce programmable output values of impedance pulses.

24. An implantable device as set forth in claim 15 and wherein the impedance measurement is switchable between more than two electrodes to obtain best position for signal to noise.

25. An implantable device as set forth in claim 15 having additional impedance circuit electrodes, at least one of which is adapted to be located in an appendage or near the heart.

26. An implantable device as set forth in claim 15 wherein said device housing additionally houses or communicates with an implanted device of the kind listed: Pacemaker, Implantable Defibrillator, Drug pump, Loop ECG recorder, hemodynamic paramater recorder/monitor.

27. Apparatus for implant into a living body having at least one lead adapted for location in the heart of said body and means for generating electrical output between said at least one lead and another electrode so as to enable the measurement of impedance between said at least one lead and said other electrode, the improvement comprising means to determine the impedance of the thoracic cavity of the body based on the value of impedance measured between said lead and said electrode, and means to determine a value representing a level of edema based on said measurement wherein said means for interpreting comprises LTA/STA determining circuit means wherein a processor circuit derives a LTA signal value and a STA signal value based on the values of impedance stored over a predefined long term and short term, respectively for determining an LTA value and an STA value and memory means for storing said determined LTA and STA values and LTA/STA updating circuit means for updating said STA and LTA values based on new measurements of impedance.

28. Implantable apparatus and system having monitor means for determining edema values and to record such values and having at least one additional value monitor means for monitoring physiologic values from a list of physiologic parameters comprising:

activity, activity per unit of time, activity variability, heart rate, heart rate variability, respiration, minute ventilation, pulmonary edema, transthoracic edema, local edema, variability in edema, arrhythmia senses, frequency of arrhythmia senses, duration of arrhythmia episodes, long term values of preceding sense values, pressure values, blood oxygen, or patient activation temporal markers.

29. Device as set forth in claims 1 or 15 and 28 further comprising:

communications means for transmitting said values to an external device.

30. Device as set forth in claims 1, 15 or 28 and further having an associated base station for periodically monitoring, for storing or retransmitting, output data transmitted by said device.

31. Device as set forth in claims 1, 15 or 28 and further having an associated base station for periodically monitoring, for storing or retransmitting, output data transmitted by said device said base station further comprising a connection circuit to telephonically link and to send said data to a monitor system at a remote location.

32. Device as set forth in claims 1, 15 or 28 and further having an Activation device having patient triggerable means activatable outside a patient's body to cause the implanted device to output data so as to enable storing data and wherein said implant device further comprises an update trigger circuit means to start record over when signal indicating data was properly received is given.

33. A device as set forth in claim 1 further comprising a therapy activation circuit for activating drug therapy responsive to impedance value changes.

34. A method of determining patient pulmonary edema comprising:
   measuring impedance between two electrodes implanted within a patient's body a multiplicity of times throughout a chronic period greater than a day,
   filtering cyclic body effects on the impedance signal value from the signal to generate a DC signal value for each said measurement step,
   storing a history of filtered impedance changes representative of changes in said DC impedance signal value within said patient in an implanted device, and
   determining a level of edema based on said changes in said DC impedance signal values that have occurred during said monitored history.

35. An implantable medical device for chronic implant into a living body having at least two electrodes exposed to tissue within said body and pulse generator means for generating electrical output so as to provide for measurement of impedance between said at least two electrodes, the improvement comprising
   impedance determination means to determine the impedance of the thoracic cavity of the body based on the dc value of impedance measured between said two electrodes,
   means to determine values representing a level of edema based on said measurement at times over a course of days, and
   means for storing said value representing a level of impedance in said device for said times over said course of days.

36. An implantable device as set forth in claim 35 having additional impedance circuit electrodes, at least one of which is adapted to be located in an appendage or near the heart.

* * * * *